United States Patent [19]

Aliotta et al.

[11] 4,235,631

[45] Nov. 25, 1980

[54] CORROSION-RESISTANT DENTAL ALLOY HAVING IMPROVED HANDLING CHARACTERISTICS

[75] Inventors: Joseph Aliotta, Newton, Mass.; Louis F. Alcuri, Jr., Matawan, N.J.

[73] Assignee: Engelhard Minerals & Chemicals Corporation, Iselin, N.J.

[21] Appl. No.: 936,667

[22] Filed: Aug. 24, 1978

Related U.S. Application Data

[63] Continuation-in-part of Ser. No. 760,181, Jan. 17, 1977, abandoned.

[51] Int. Cl.³ .............................. B22F 1/00; B22F 9/00
[52] U.S. Cl. .................................... 75/251; 75/0.5 R; 148/13.1
[58] Field of Search ...................... 75/0.5 R, 251, 255, 75/169, 173 C, 134 N, 134 B, 134 C; 148/13.1

[56] References Cited

U.S. PATENT DOCUMENTS

| | | | |
|---|---|---|---|
| 3,841,860 | 10/1974 | Wolf | 75/169 |
| 3,871,876 | 3/1975 | Asgar et al. | 75/169 |
| 3,980,472 | 9/1976 | Asgar et al. | 75/173 C |
| 3,997,327 | 12/1976 | Tolliver et al. | 75/169 |
| 3,997,328 | 12/1976 | Greener | 75/0.5 R |
| 3,997,329 | 12/1976 | Aliotta et al. | 75/169 |
| 3,997,330 | 12/1976 | Aliotta et al. | 75/169 |
| 4,008,073 | 2/1977 | Kropp | 75/169 |
| 4,080,199 | 3/1978 | Sung et al. | 75/0.5 R |

*Primary Examiner*—L. Dewayne Rutledge
*Assistant Examiner*—Michael L. Lewis

[57] ABSTRACT

A corrosion-resistant dental alloy shows improved handling characteristics during the filling of a dental cavity with an amalgam of the alloy. The alloy particles comprise a mixture of silver, tin and copper particles having a mean particle size of between about 20 and 26.5 microns, and further having a particle size distribution such that substantially all of the particles fall within a particle size range of from about 10 to 52 microns. The particles have a surface area ranging between about 0.22 $m^2/gm$ and 0.31 $m^2/gm$. The alloy, after amalgamation with mercury, retains a corrosion resistance comparable to that of spherical particles having substantially the same composition and having a surface area of about 0.21 $m^2/gm$, while retaining handling characteristics comparable to those of flake-like particles also having substantially the same composition and having a surface area of at least about 0.33 $m^2/gm$. The copper and silver content of the particles may be higher at their surface than in the interior thereof.

13 Claims, 4 Drawing Figures

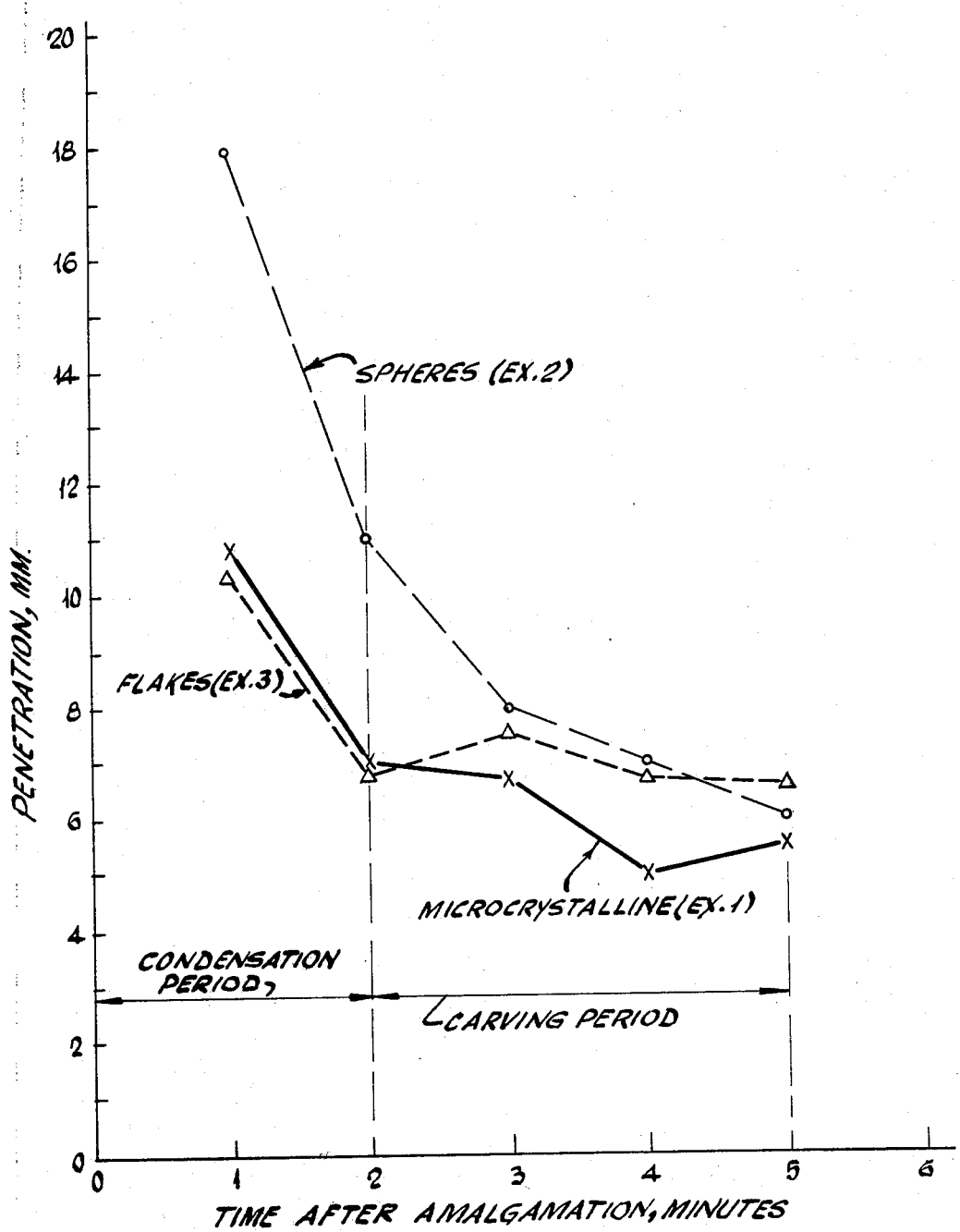

CORROSION-RESISTANT DENTAL ALLOY HAVING IMPROVED HANDLING CHARACTERISTICS

CROSS REFERENCE TO RELATED APPLICATIONS

This application is a continuation-in-part of copending application Ser. No. 760,181 filed Jan. 17, 1977 now abandoned.

BACKGROUND OF THE INVENTION

The invention relates generally to the dental alloys which are used for filling teeth from which decayed portions have been removed. More particularly, the invention relates to an improved dental alloy having both corrosion resistance and improved handling characteristics compared to alloys of the prior art.

The prior art emphasized the development of alloys which are corrosion resistant. While typical dental alloys are principally composed of silver and tin, they usually contain small amounts of copper and zinc. A typical alloy of the prior art would contain at least 65 wgt. % silver, about 1–2 wgt. % zinc, and about 2–4 wgt. % copper, with the remainder being tin. Such alloys are not completely resistant to corrosion. It has been found that increasing the copper content of such alloys provides increased strength and also avoids the formation of what is known in the art as the gamma-two phase, a tin and mercury phase which has low resistance to corrosion and thus may lead to early deterioration of fillings. Typical of such high copper alloys are those disclosed in U.S. Pat. No. 3,871,876 and U.S. Pat. No. 3,997,328. Such dental alloy compositions increase the copper content from the typical 2–4 wgt. % to the range of 8–27 wgt. % in the first-mentioned patent, and in the latter patent from 20–40 wgt. %.

While such alloys have improved corrosion resistance, another important characteristic of dental alloys is its handling characteristics. The success of a dentist in filling a dental cavity is related to the handling characteristics of the alloy after it is amalgamated with mercury. For example, the high copper alloy disclosed in U.S. Pat. No. 3,871,876 is typically produced by air atomization from the molten state which results in a spherical or spheriodal form for the finished alloy. It is characteristic of alloys having a spherical shape that they feel relatively soft to the dentist and appear to require delicate handling. They are sometimes difficult to pack into a dental cavity since they have a tendency to be forced up the wall of the cavity if too much pressure is exerted or an instrument is used which has too small a bearing area. Consequently, many dentists find that such spherical material is not well adapted to their individual technique. As a result, they may be unable to take advantage of the corrosion resistance inherent with spherical alloys having a high copper content.

One method of improving handling characteristics of conventional dental alloys is disclosed and claimed in U.S. Pat. No. 3,997,327. In that invention a major portion of spherical particles is combined with a minor portion of microcut irregular particles, or flakes. Typical dental alloys in the prior art generally have been of the flake type, which inherently requires a higher pressure in order to be packed into a dental cavity than is characteristic of the spherical particle type alloys. By combining spherical particles with flake particles having the same composition, it is possible to improve the handling characteristics of the resulting mixture. Such a combination, having a conventionally low copper content, has less resistance to corrosion than the higher copper content alloys previously discussed.

One object of the present invention is to provide improved handling characteristics to corrosion-resistant dental alloys.

SUMMARY OF THE INVENTION

In accordance with the present invention, there is provided a corrosion-resistant dental alloy in particulate form for use as a filling for dental cavities after amalgamation with mercury and comprising a mixture of silver, tin and copper. The alloy consists essentially of particles having a mean particle size of between about 20 and 26.5 microns, and having a particle size distribution such that substantially all of the particles fall within a particle size range of from about 1 to 75 microns. The particles further have a surface area ranging from about 0.22 $m^2$/gm to 0.31 $m^2$/gm, so that the alloy, after amalgamation, retains a corrosion resistance comparable to that of spherical particles having substantially the same composition and having a surface area of about 0.21 $m^2$/gm, while retaining handling characteristics comparable to those of flake-like particles also having substantially the same composition and having a surface area of at least about 0.33 $m^2$/gm.

In one aspect of the invention, the particles have a surface area ranging between about 0.23 $m^2$/gm and 0.26 $m^2$/gm. The composition of the alloy may advantageously comprise from about 47 to 70 percent by weight of silver, from about 20 to 32 percent by weight of tin, and from about 7 to 27 percent by weight of copper. In one aspect of the invention, at least about 90% by weight of the particles have a particle size range of from about 10 to 52 microns.

In another aspect, the invention provides a corrosion-resistant dental alloy in particulate form for use as a filling for dental cavities after amalgamation with mercury, comprising a mixture of silver, tin and copper. The alloy comprises particles having a surface area at least about 20 to 30 percent greater than the surface area of spherical particles but less than about 0.33 $m^2$/gm, so that the alloy, after amalgamation, retains a corrosion resistance comparable to that of spherical particles having substantially the same composition and having a surface area of about 0.21 $m^2$/gm, while retaining handling characteristics comparable to those of flake-like particles also having substantially the same composition and having a surface area of at least about 0.33 $m^2$/gm.

In accordance with the present invention there is also provided a corrosion-resistant dental alloy adapted for amalgamation with mercury, which alloy, after amalgamation, retains a corrosion-resistance comparable to that of spherical particles having substantially the same composition, and further retains handling characteristics comparable to those of flake-like particles.

BRIEF DESCRIPTION OF THE DRAWINGS

FIG. 2 plots the results of tests described herein and applied to several dental amalgams.

DESCRIPTION OF THE PREFERRED EMBODIMENTS

Figure 1A:
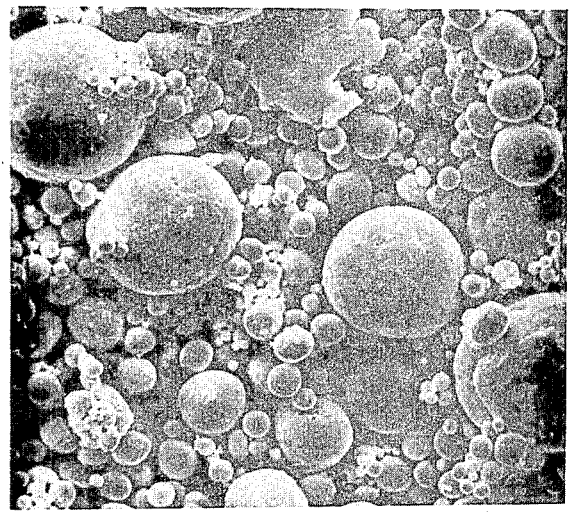
FIG. 1a shows the spherical particles of the prior art corresponding to U.S. Pat. No. 3,871,876.

A dentist, in packing an amalgam prepared from a dental alloy and mercury into a dental cavity considers two handling factors to be of particular importance. The first handling characteristic may be termed "condensation" and relates to the resistance of the alloy to being packed into the cavity by the dentist using typical instruments. It will be clear that an amalgam must have sufficient plasticity when under pressure to enable it to flow into and completely fill all portions of the cavity, thereby preventing the formation of open spaces in the finished filling which could weaken it or permit further decay to the tooth structure. At the same time, the amalgam must not be so fluid as to flow out from beneath the dental instruments during condensation of the amalgam and move up the wall of the cavity. In such situations, a non-uniform degree of packing necessarily results, with poor adaptation to the cavity and increased porosity which weakens the filling and may result in further decay. Thus, one important handling characteristic of an amalgam is its ability to be pressed into a dental cavity to fill all the small openings under the desired condensation pressure, while not being so soft that the dentist cannot adequately compact the amalgam. This condensation pressure may be approximated by an empirical test which will be hereinbelow described and which is useful in connection with the present invention.

The second handling characteristic of importance to the dentist is the ability of an amalgam to be carved or shaped in order to finish the exterior surface of the compacted filling. An amalgam also must be of a desired plasticity in order to be satisfactorily carved or shaped. An amalgam which may be satisfactorily packed into a dental cavity may be difficult to smooth and shape when the packing process is completed. On the other hand, an amalgam which is easy to carve and shape may be difficult to pack properly into a dental cavity. The carving characteristic of amalgams derived from various dental alloys may be approximated by another empirical test to be described hereinbelow.

The dental alloy of the invention combines corrosion resistance and good handling characteristics. When amalgamated with mercury, the alloy particles of the invention have handling qualities generally similar to those of flake particles. Its corrosion resistance is enhanced in that it has a relatively high copper content. Its composition corresponds generally to that of the spherical material disclosed in U.S. Pat. No. 3,871,876 and, as is true of the U.S. Pat. No. 3,871,876, the particles may have a higher than average silver and copper content at the surface of the particles than in the interior thereof.

The alloy of the present invention is produced in a non-spherical irregular shape rather than the spherical form of the U.S. Pat. No. 3,871,876, but one which differs from the irregular flake-like particles typical of the prior art. The alloy particles according to the present invention characteristically have a surface area of about 0.23–0.26 $m^2/gm$, which is 20–30% greater than the surface area of typical spherical particles of the same composition and about 20–30% less than typical flake-like particles of the same composition. The particles of the invention may be produced by a variant of the air atomization process used to form spherical particles, although other techniques may be used.

Figure 1C:
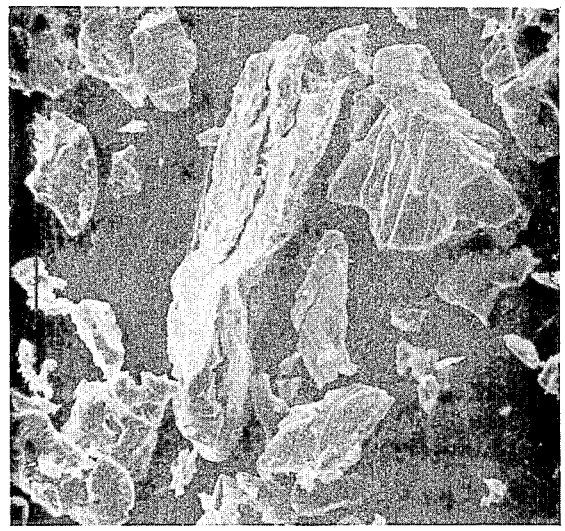
FIG. 1c shows particles corresponding to microcut or flake-like particles of the prior art.
Figure 1B:
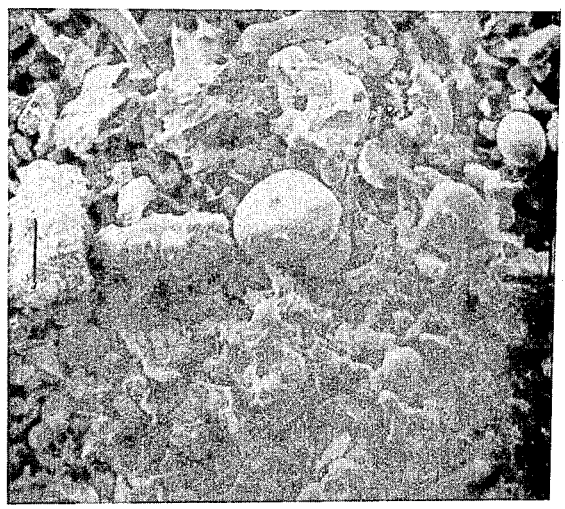
FIG. 1b shows particles corresponding to a dental alloy of the present invention.

As described in U.S. Pat. No. 3,253,783 and elsewhere the gas atomization technique may be used to produce spherical or spheroidal particles from molten dental alloys. Particles are screened after cooling to provide a powdered alloy having particles in the size range of about 1 micron to about 65 microns. Larger and smaller particles are separated and recycled to be remelted and recast. Spherical particles of the prior art, such as are illustrated in FIG. 1a, have an average surface to mass ratio of about 0.21 $m^2/gm$ as measured by the usual BET apparatus. Flake alloys of the prior art of approximately the same size as the spherical particles are illustrated in FIG. 1c and are substantially different, having a surface to mass ratio of about 0.33 $m^2/gm$. A mixture of spherical particles with flake particles as disclosed in U.S. Pat. No. 3,997,327 will have a surface to mass ratio between the two extremes. Rather than mixing spherical and flake particles, the alloy of the present invention is preferably produced in a single step process to provide a new particle shape. The air atomization technique or other microcasting method may be altered to cause distortion of the particles, which otherwise freeze in a spherical or spheroidal shape. A suitable morphology in accordance with one embodiment of the invention is illustrated in FIG. 1b. The spherical form of FIG. 1a is no longer predominant. Neither do the particles have the distinctive shape of microcut, flake-like particles, as seen in FIG. 1c, nor do they have the striations characteristic of such particles. In the specification and claims all surface area measurements are those as measured by known BET apparatus, and are much larger than geometric surface areas due to surface roughness and porosity. For the alloy particles, geometric surface area may be approximated by subtracting about 90% from the BET value.

The alloy particles according to the invention need not be exactly the same as those of FIG. 1b. Rather, the particles of the invention may be characterized by their surface area and the handling characteristics measured as hereinbefore described. Typically, particles of the invention will have a surface area within the range of 0.22 to 0.31 $m^2/gm$ and preferably in the range of 0.23 to 0.26 $m^2/gm$. Specifically, the particles from which the data of FIG. 2 is derived have a median surface area of about 0.24 $m^2/gm$. It should be noted that the surface area is related in part to the particle size, thus the values given herein relate to a particle size distribution suitable for dental alloys and as specifically reported hereinafter for the alloy of the invention.

It should be further noted that the surface area measured by the BET apparatus is much larger than the geometric exterior surface of the particles. For example, a perfect sphere would have a surface area only about 10% of that measured for the generally spherical particles of FIG. 1a. The additional 90% of the measured surface is evidently due to surface roughness and porosity. Since this additional surface seems less likely to have a large effect on the handling properties of amalgams than the geometric surface, the geometric surface of the particles should be compared rather than the BET surface. However, the geometric surface has not been measured although it may be approximated by subtracting about 90% of the BET value for comparison purposes.

Amalgams are produced by mixing mercury with dental alloys of the invention. At the completion of the amalgamation process, the amalgam is condensed into a tooth cavity by a dentist and then the filling is carved or shaped until the amalgam has become so hard that it cannot be worked. This period is typically about six minutes. The dentist packs or condenses the amalgam into the tooth cavity while the amalgam is still soft enough to do so. The pressure required is quite important to the dentist as has been previously discussed and to characterize dental alloys of the invention we have chosen to designate the resistance of the amalgam one minute after amalgamation is complete as the condensation factor. A lower value indicates that an amalgam is stiffer and requires more pressure to pack or condense it into a tooth cavity than an amalgam having a higher numerical value.

The test used to obtain values reported herein for condensation factors may be described as follows. A pellet of dental alloy is mixed with the recommended amount of mercury in an amalgamator for the manufacturer's recommended time. A commercially available Wig-L-Bug Model 5AR manufactured by Crescent Corporation was used in the tests reported herein, although other amalgamators would be acceptable. After the amalgamation is complete, the amalgam is immediately placed on a flat glass plate and covered by another such glass plate and pressed to a one millimeter thickness, as determined by one millimeter spacers placed between the plates. The top plate is removed and measurements are made of the resistance of the flattened amalgam disc during the hardening period. For the measurements reported herein an Instron testing unit model 1101 produced by Instron Corporation was employed. A constant load of five pounds was placed on a two millimeter steel ball in contact with the amalgam. The depth of the indentation made by the ball when the load was applied for fifteen seconds is used as a measure of the resistance of the amalgam. Tests were made at one minute intervals for a period of five minutes, or until no further change in the resistance was measured. The period of time during which measurements were made approximates the time which a dentist uses to fill a tooth cavity and to carve the filling. Test results obtained with prior art dental alloys in spherical and flake form are compared with the dental alloy of the invention in the examples below.

The carvability factor relates to the ability of a hardening dental amalgam to be carved and shaped by dental instruments after it has been compacted. It will be apparent that after the compaction or condensation period (about 2 minutes) the dentist will have a limited time in which to shape or carve the hardening amalgam. A variant of the test previously described is used to obtain a carving factor. The two millimeter ball loaded by a five pound weight is replaced with a one pound Gilmore needle having a one millimeter point. The Gilmore needle is normally used for measuring setting rates of cements and plastic materials and has been described in an article by Peyton and Craig in *Restorative Dental Materials,* 4th ed., 1971. It has been found that the lighter loaded Gilmore needle will fail to penetrate an amalgam after it is sufficiently hardened. The time between the end of the amalgamation process and the failure of the Gilmore needle to penetrate the hardening amalgam may be used as an index of the carvability of the amalgam.

EXAMPLE 1

A dental alloy is prepared by mixing individual metal powders and resulting in an overall composition 58 wt. % Ag, 29 wt. % Sn, 13 wt. % Cu. The powdered mixture is melted and processed in an air atomization apparatus modified to minimize the formation of spherical particles by contacting the molten droplets during the cooling process, thereby producing the randomly-shaped microcrystalline particles of the invention. The particles formed have a surface area of 0.24 $m^2$/gm. They are sieved to produce a powdered alloy according to the invention as shown in FIG. 1b and having particles sized within the range of 1 micron to 45 microns. The powdered alloy is then pelleted and mixed with sufficient mercury to form an amalgam having an alloy to mercury ratio of 1:1. The amalgam is measured for its resistance to condensation pressure according to the test hereinbefore described and the results plotted on FIG. 2.

EXAMPLE 2

A dental alloy is prepared by mixing individual metal powders and resulting in an overall composition 58 wt. % Ag, 29 wt. % Sn, 13 wt. % Cu. The powdered mixture is melted and processed in an air atomization apparatus according to U.S. Pat. No. 3,871,876 to produce spherical particles as shown in FIG. 1a. The particles have a surface area of 0.21 $m^2$/gm. After sieving, the particles are within the range of 1 micron to 40 microns. The powdered alloy is then pelleted and mixed with sufficient mercury to form an amalgam having an alloy to mercury ratio of 1:1. The amalgam is subjected to the condensation factor test described hereinbefore and the results plotted in FIG. 2.

EXAMPLE 3

A dental alloy is prepared by mixing individual metal particles and resulting in an overall composition 68 wt. % Ag, 27 wt. % Sn, 4.4 wt. % Cu, 0.6 wt. % Zn. The powdered mixture is melted and cast into a bar, from which it is cut on a lathe into flake-like particles as shown in FIG. 1c according to the usual technique of the prior art. The particles have a surface area of 0.33 $m^2$/gm. After sieving, the particles are within the range of 2 microns to 50 microns. The powdered alloy is then pelleted and mixed with sufficient mercury to form an amalgam having an alloy to mercury ratio of 1.2:1. The amalgam is subjected to the condensation factor test described hereinbefore and the results plotted in FIG. 2.

As shown in FIG. 2 flake-like alloys of the prior art (FIG. 1c and Example 3) are firmer when freshly amalgamated than amalgams made with spherical particles. Amalgams made with flake particles require heavier pressure when being condensed or packed into a tooth cavity. The condensation factors expressed as millimeters of indentation after one minute from completion of the amalgamation process are 10.75, 18, and 10.3 for the alloys of Examples 1-3 respectively. The spherical particles of Example 2 and FIG. 1a produce an amalgam which is soft when freshly mixed with mercury. As previously indicated dentists often find amalgams made with spherical particles to be delicate to handle and difficult to condense properly. The alloy of the invention (FIG. 1b and Example 1) has a unique morphology and is neither spherical nor flake-like. The handling characteristics are similar to those of the flake-like particles of the prior art during the condensation of the amalgam into a tooth cavity.

The carving period (typically 2 to 5 minutes after amalgamation) represents the time period when the dentist shapes the compacted filling to suit the patient's bite. After a certain period the amalgam becomes unduly hard and can no longer be worked with the usual dental instruments. After about one hour a typical amalgam has reached substantial strength and can withstand the pressure of normal use. As is indicated by FIG. 2, the effect of particle size on the handling characteristics of amalgams is more significant during the condensation period than during the carving period. In fact, one might conclude from FIG. 2 that amalgams made according to the invention would be more difficult to carve than those made with either spherical or flake-like particles. However, measurements of amalgams made of the three types of particles in the preceding examples were made by substituting a Gilmore needle for the two millimeter ball as previously described, with the following results.

TABLE I

| Particle Type | Carving Factor Time, minutes - Penetration Ceased |
|---|---|
| Spherical (Ex. 2) | 4.15 |
| Microcrystalline (Ex. 1) | 3.15 |
| Flake (Ex. 3) | 2.15 |

The above results indicate that spherical particles can be carved with less force and for a longer time than the randomly-shaped microcrystalline particles of the invention, which in turn can be carved with less force than the flake-like particles.

As previously discussed, the alloy of the invention may be produced by modification of the air atomization process so that molten metal is distorted instead of frozen into spherical form. Such particles may be produced by other processes, for example, by splat-cooling of a stream of molten alloy and by modifying the conventional metallizing process. However produced, the particles will have a surface area intermediate that of spheres and that of flakes in the preferred form characterized by having a surface area of 0.23–0.26 m$^2$/gm, which is 20–30% greater than the typical spherical particle and 20–30% less than the typical flake-like particles.

The composition will be within the range of about 47% to 70% by weight silver, 20% to 32% by weight tin, and 7% to 27% by weight copper which corresponds to that of the spherical particles of U.S. Pat. No. 3,871,876. It has been found that the alloy in the unique form of the invention still has corrosion resistance as measured by the anodic polarization test described in U.S. Pat. No. 3,997,329, even though the particles are no longer spherical in form. The anodic polarization test indicates by the absence of the gamma-two phase that the amalgam is resistant to corrosive attack. It is believed that the higher than average silver and copper content found at the surface of the irregular particles of the invention as well as in the spherical particles of U.S. Pat. No. 3,871,876 is related to the relatively high copper content of the alloy and the speed at which it is cooled from the molten state. It is expected that many methods of forming particles from molten metal which involve rapid cooling can be employed.

Although no explanation is presently available, it has been found that if the alloy of the invention is prepared as a mixture of about 60% by weight spheres and about 40% by weight flakes having the same composition, the handling properties are similar to that of particles of the invention, but the amalgam is no longer corrosion resistant by the anodic polarization test. However, with their unique morphology the particles of the invention unexpectedly combine both corrosion resistance and improved handling characteristics.

After the particles have been produced, they are sieved to provide a typical particle size distribution as follows:

| Microns | Wt. % |
|---|---|
| 52–75 | 0.3 to 1.4 |
| 44–52 | 1.4 to 12.2 |
| 38–44 | 1.6 to 8.9 |
| 30–38 | 20.9 to 24.6 |
| 20–30 | 26.1 to 35.7 |
| 10–20 | 24.0 to 35.4 |
| 1–10 | 3.6 to 7.2 |

The mean particle size is typically 20 to 26.5 microns. Although some variation about the above typical size distribution may be made to adjust the handling characteristics, an amalgam prepared with particles having a significantly different size distribution from that given above will have handling characteristics differing from those reported herein. In general, the smaller the average particle size, the firmer the amalgam will be and the shorter the working time.

As previously discussed, the surface area of the alloy particles of the invention having the size distribution as given above will be found to have a surface to volume ratio of about 0.23–0.26 m$^2$/gm. With other size distributions, the surface to volume ratio may be as wide as 0.22 to 0.32 m$^2$/gm.

Particles may be used directly to form amalgams, especially if employed in pre-mixed dental capsules. Often the particles are pelletized for use in dispensers designed to provide the desired amount of mercury needed to amalgamate with the pelleted alloy. The pelletizing process has been found to alter the handling properties of the resulting amalgam, generally providing a dry and less plastic amalgam than if the powdered alloy were used directly. It has been found that by heat treating the pellets in a vacuum for a suitable time, the mechanical properties and useful working time of the alloy can be returned to their original and more desirable values. Typically a vacuum of about ten microns (0.01 mm Hg absolute pressure) has been found to be acceptable, the determining factor being the need to avoid oxidation of the metals with the consequent degradation of physical properties and corrosion resistance. The heat treatment is carried out typically between 100° and 700° F. (37.8° to 370° C.) as required until the handling characteristics of an amalgam made from the pellets matches those of the unpelleted powder, as measured by the condensation and carving factors.

Generally, at least about 90% of the particles of the alloy of the invention will fall within the size range of from about 10 to 52 microns. Particles of a size greater than 52 microns should comprise not more than about 1.4% by weight of the alloy particles. With particles larger than about 52 microns. Such oversized particles could pose difficulties in filling small apertures in a tooth. The lower limit of particle size is determined by the fact that with very small particle sizes the desired effect provided by the defined specific shape of the particles of the invention is lost. Further, very fine particle sizes of the alloy use up a proportionately greater amount of mercury in the amalgam and tend to increase the proportion of mercury beyond the desired limit.

Obviously, particle range sizes expressed herein are maximum ranges; the actual particle size range of specific embodiments of the invention may fall within a narrower range encompassed by the broadly states ranges.

The foregoing discussion of the preferred embodiments of the invention is not intended to limit the scope of the invention, which is defined by the claims which follow.

What is claimed is:

1. A corrosion-resistant dental alloy in particulate form for use as a filling for dental cavities after amalgamation with mercury, comprising a mixture of silver, tin and copper, said alloy consisting essentially of randomly shaped particles having a mean particle size of between about 20 and 26.5 microns, and further having a particle size distribution such that substantially all of said particles fall within a particle size range of from about 1 to 75 microns, said particles having a surface area which, exclusive of both spherical particles and flake-like particles as defined below, ranges from 0.22 $m^2/gm$ to about 0.31 $m^2/gm$, so that said alloy, after amalgamation, retains a corrosion resistance comparable to that of spherical particles having substantially the same composition and having a surface area of about 0.21 $m^2/gm$, but in any event, less than 0.22 $m^2/gm$, while retaining handling characteristics comparable to those of flake-like particles also having substantially the same composition and having a surface area of at least about 0.33 $m^2/gm$ and approximately the same particle size and distribution as said randomly shaped particles.

2. The corrosion-resistant dental alloy of claim 1 wherein said particles have a surface area ranging between about 0.23 $m^2/gm$ and 0.26 $m^2/gm$.

3. The corrosion-resistant dental alloy of claim 1 in combination with mercury to provide a dental amalgam.

4. The corrosion-resistant dental alloy of claim 1 in combination with about 1 part by weight of mercury for each part by weight of said corrosion-resistant dental alloy.

5. The corrosion-resistant dental alloy of claim 1 wherein said mixture of silver, tin and copper comprises from about 47 to 70 percent by weight of silver, from about 20 to 32 percent by weight of tin, and from about 7 to 27 percent by weight of copper.

6. The corrosion-resistant dental alloy of claim 1 wherein at least about 90% by weight of said particles fall within a particle size range of from about 10 to 52 microns.

7. A corrosion-resistant dental alloy in particulate form for use as a filling for dental cavities after amalgamation with mercury comprising a mixture of silver, tin and copper, said alloy consisting essentially of randomly shaped particles which, exclusive of both spherical particles and flake-like particles as defined below, have a surface area at least about 20 percent greater than the surface area of spherical particles but less than about 0.33 $m^2/gm$, whereby said alloy, after amalgamation, retains a corrosion resistance comparable to that of spherical particles having substantially the same composition and having a surface area of about 0.21 $m^2/gm$, but in any event, less than 0.22 $m^2/gm$, while retaining handling characteristics comparable to those of flake-like particles also having substantially the same composition and having a surface area of at least about 0.33 $m^2/gm$ and approximately the same particle size and distribution as said randomly shaped particles.

8. The corrosion-resistant dental alloy of claim 7 wherein said mixture of silver, tin and copper comprises from about 47 to 70 percent by weight of silver, from about 20 to 32 percent by weight of tin and from about 7 to 27 percent by weight of copper.

9. The corrosion-resistant dental alloy of claim 7 having a surface area of less than about 0.31 $m^2/gm$.

10. The corrosion-resistant dental alloy of claim 7 wherein said alloy particles have a mean particle size of between about 20 and 26.5 microns, and further wherein said particles have a particle size distribution such that substantially all of said particles fall within a particle size range of from about 1 to 72 microns.

11. The corrosion-resistant dental alloy of claim 10 wherein at least about 90% by weight of said particles fall within a particle size range of from about 10 to 52 microns.

12. The corrosion-resistant dental alloy of claim 7 wherein said alloy particles have a surface area at least about 30 percent greater than the surface area of spherical particles.

13. The corrosion-resistant dental alloy of claim 7 wherein said alloy particles have a surface area which is about 20–30 percent greater than the surface area of spherical particles but less than about 0.33 $m^2/gm$.

* * * * *